(12) United States Patent
Jiang et al.

(10) Patent No.: US 6,458,974 B1
(45) Date of Patent: Oct. 1, 2002

(54) SYNTHESIS OF β-LAPACHONE AND ITS INTERMEDIATES

(75) Inventors: Zhiwei Jiang, Grafton, MA (US); Jane Hogeland, Woburn, MA (US)

(73) Assignee: Cyclis Pharmaceuticals, Inc., Norwood, MA (US)

( * ) Notice: Subject to any disclaimer, the term of this patent is extended or adjusted under 35 U.S.C. 154(b) by 0 days.

(21) Appl. No.: 09/957,260

(22) Filed: Sep. 19, 2001

Related U.S. Application Data

(60) Provisional application No. 60/264,116, filed on Jan. 25, 2001.

(51) Int. Cl.[7] .............................................. C07D 311/92
(52) U.S. Cl. ........................ 549/389; 390/391; 390/393
(58) Field of Search ................................ 549/389, 390, 549/391, 393

(56) References Cited

U.S. PATENT DOCUMENTS 5,969,163 A * 10/1999 Frydman et al. ............ 549/389

OTHER PUBLICATIONS

Fieser, L, 1927, Journal of American Chemical Society, 49, 857–804.*
Planchon, et al. (1995). *Cancer Res.* 55: 3706–3711.
Li, et al. (1995). *Cancer Res.* 55: 3712–3715.
Weller, et al. (1997). *Int. J. Cancer 73*: 707–714.
Wuertzberger, et al. (1998). *Cancer Res.* 58: 1876–1885.
Li, et al. (1999). *Proc. Natl. Acad. Sci. USA* 96(23): 13369–13374.
Boothman, et al., (1987). *Cancer Res.* 47: 5361–5366.
Boorstein, et al. (1983). *Biochem Biophys. Commun.* 117: 30–36.
Schaffner–Sabba, et al. (1984). *J. Med. Chem.* 27(8): 990–994.
Li, et al. (1993). *J. Biol.Chem.* 268(30): 22463–24468.
Amaral, et al. (1992).*J. Heterocyclic Chem.* 29: 1457–1460.
Lai, et al. (1995). *Histol. Histopathol.* 13: 89–97.
Huang, et al. (1999). *Mol. Med.* 5: 711–720.
Li (1999). *Mol. Med.* 5: 232–239.
Li, et al. (2000). *Mol. Med.* 6: 1008–1015.
Sun, et al. (1998). *Tetrahedron Letters* 39: 8221–8224.

* cited by examiner

*Primary Examiner*—Ceila Chang
*Assistant Examiner*—Andrea D. Small
(74) *Attorney, Agent, or Firm*—Barry J. Marenberg; Ivor R. Elrifi; Mintz, Levin, Cohn, Ferris, Glovsky and Popeo, P.C.

(57) ABSTRACT

A novel process for synthesizing β-lapachone (beta-lapachone), an agent that has demonstrated significant antineoplastic activity against human cancer lines. The process comprises the conversion of starting material, 2-hydroxy-1,4-naphothoquinone into β-lapachone intermediate, lapachol. The lapachol is then converted to β-lapachone by treatment with sulfuric acid and purified by recrystallization from ethanol. This novel process is extremely simple and provides β-lapachone in excellent quality and high yield.

15 Claims, 5 Drawing Sheets

SYNTHESIS OF β-LAPACHONE AND ITS INTERMEDIATES

RELATED APPLICATION

The present application claims priority under 35 U.S.C. §120 to U.S. provisional patent application serial No. 60/264,116, which was filed on Jan. 25, 2001, and which is incorporated by reference herein in its entirely.

FIELD OF THE INVENTION

The present invention is directed to a process for the synthesis of β-lapachone (Beta-lapachone) and lapachol, the β-lapachone (Beta-lapachone) intermediate, which are important agents in cancer chemotherapy.

BACKGROUND OF THE INVENTION

Over 1.22 million new cancer cases will be diagnosed in the U.S. in the year 2001 alone. With more than 563,000 deaths annually, cancer is the second leading cause of death behind heart disease (UBS Warburg "Disease Dynamics: The Cancer Market", Nov. 8, 2000). Surgery and radiotherapy may be curative if the disease is found early, but current drug therapies for metastatic disease are mostly palliative and seldom offer a long-term cure. Even with the new chemotherapies entering the market, improvement in patient survival is measured in months rather than in years, and the need continues for new drugs effective both in combination with existing agents as first line therapy and as second and third line therapies in treatment of resistant tumors.

As a single agent, β-lapachone has demonstrated significant antineoplastic activity against human cancer cell lines at concentrations typically in the range of 1–10 μM ($IC_{50}$). Cytotoxicity has been demonstrated in transformed cell lines derived from patients with promyelocytic leukemia (Planchon et al., *Cancer Res.*, 55 (1996) 3706), prostate (Li, C. J., et al., *Cancer Res.*, 55 (1995) 3712), malignant glioma (Weller, M. et al., *Int. J. Cancer*, 73 (1997) 707), hepatoma (Lai, C. C., et al., *Histol Histopathol*, 13 (1998) 8), colon (Huang, L., et al., *Mol Med*, 5, (1999) 711), breast (Wuertzberger, S. M., et al., *Cancer Res.*, 58 (1998) 1876), ovarian (Li, C. J. et al., *Proc. Natl. Acad. Sci. USA*, 96(23) (1999) 13369–74), pancreatic (Li, Y., et al., *Mol Med*, 6 (2000) 1008; Li, Y. Z., *Mol Med*, 5 (1999) 232), and multiple myeloma cell lines, including drug-resistant lines (Li, Y., *Mol Med*, 6 (2000) 1008). No cytotoxic effects were observed on normal fresh or proliferating human PBMC (Li, Y., *Mol Med*, 6 (2000) 1008).

β-lapachone has been shown to be a DNA repair inhibitor that sensitizes cells to DNA-damaging agents including radiation (Boothman, D. A. et al., *Cancer Res*, 47 (1987) 5361; Boorstein, R. J., et al., *Biochem. Biophys. Commun.*, 117 (1983) 30). β-lapachone has also been shown to disrupt DNA replication, causing cell-cycle delays in G1 and/or S phase, inducing either apoptotic or necrotic cell death in a wide variety of human carcinoma cell lines without DNA damage and independent of p53 status (Li, Y. Z. et al (1999); Huang, L. et al.). Topoisomerase I is an enzyme that unwinds the DNA that makes up the chromosomes. The chromosomes must be unwound in order for the cell to use the genetic information to synthesize proteins; β-lapachone keeps the chromosomes wound tight, so that the cell cannot make proteins. As a result, the cell stops growing. Because cancer cells are constantly replicating and circumvent many mechanisms that restrict replication in normal cells, they are more vulnerable to topoisomerase inhibition than are normal cells.

β-lapachone (3,4-dihydro-2,2-dimethyl-2H-naphtho[1,2-b]pyran-5,6-dione), a quinone, is derived from lapachol (a naphthoquinone) which can be isolated from the lapacho tree (*Tabebuia avellanedae*), a member of the catalpa family (Bignoniaceae). Lapachol and β-lapachone have the following chemical structures:

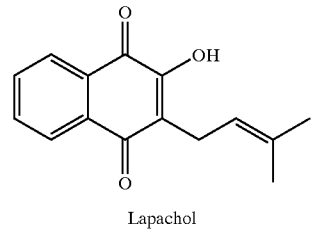

Lapachol

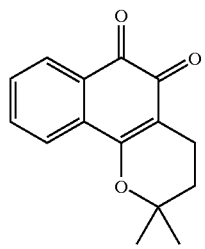

Beta-Lapachone

It is, however, both difficult and time consuming to obtain the necessary large-scale quantities of β-lapachone naturally from the lapacho tree. Although the lapacho tree is nowhere near as rare as the Pacific yew tree, from which paclitaxel (Taxol®) is derived, ensuring a sufficient quality and supply of β-lapachone from natural sources can be problematic. Numerous methods are known in the art for synthesizing β-lapachone. Two related known methods for producing lapachol, an intermediate from which β-lapachone may be synthesized are illustrated in Scheme 1.

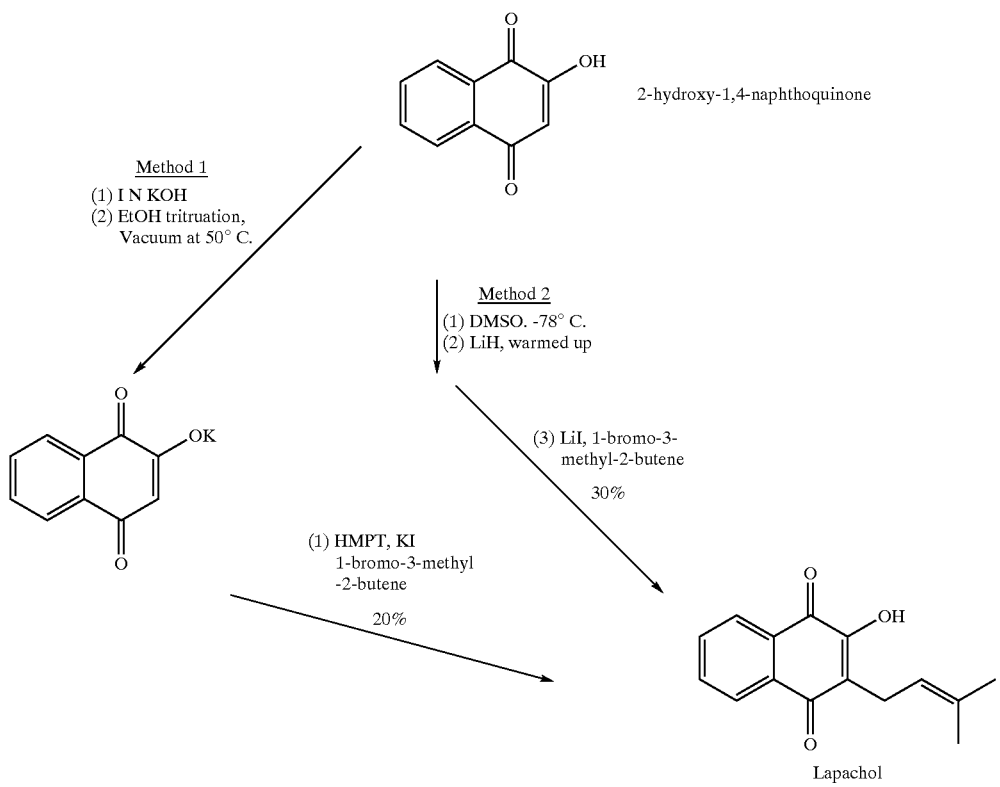

Method (1) is described in Schaffner-Sabba, K., et al., β-Lapachone: Synthesis of Derivatives and Activities in Tumor Models, *J Med. Chem.*, 27, (1984) 990–994, and is known as the potassium salt method. Method (2) is described in Sun, J. S. et al., A Preparative Synthesis of Lapachol and Related Naphthoquinones, *Tetrahedron Letters*, 39 (1998) 8221–8224), and is know as the lithium salt method. Both of these methods require the formation of a metal salt. Amaral, A., et al., in The Total Synthesis of β-lapachone, *J. Heterocyclic Chem.*, 29 (1992) 1457–1460, describes the synthesis of β-lapachone α-naphthol in eight steps and results in an overall yield of only 23%. Additionally, in U.S. Pat. No. 5,763,625, lapachol is first converted into 3-bromolapachone, which is then converted in a two-step sequence into 3-hydroxy-β-lapachone.

These known methods, however, typically provide the product in low yield, require tedious procedures or use explosive chemicals in the synthesis. Accordingly, there is a need for a process for synthesizing β-lapachone and its derivatives which is safe and simple and which produces β-lapachone and its intermediates, analogs and derivatives in high yield and excellent quality.

SUMMARY OF THE INVENTION

The present invention is directed generally to a process for the synthesis of β-lapachone and its intermediate, lapachol. More specifically, the invention is directed to process for synthesizing β-lapachone and its intermediates, derivatives and analogs, by a safe and simple process and which produces β-lapachone in high yield and high quality.

The process of the present invention teaches a novel method for the synthesis of the β-lapachone intermediate, lapachol. Lapachol is then quantitatively converted to β-lapachone and purified. Unlike the reported methods in which a metal (lithium or potassium) salt of 2-hydroxy-1, 4-naphtoquinone was prepared in situ by addition of lithium hydride or separately by addition of potassium hydroxide to the quinone solution as the first step and then reacting the metal salt with bromide compound to form lapachol, the process of the present invention eliminates this first step and commences directly with 2-hydroxy-1,4-naphthoquinone to react with 1-bromo-3-methyl-2-butene in the presence of sodium iodide and a weak base such as triethylamine, pyridine, trimethylamine, N,N-diisopropylethylamine, 2,6-lutidine, preferably triethylamine or pyridine, most preferably triethylamine, to form lapachol, a β-lapachone intermediate from which β-lapachone is subsequently synthesized.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

DETAILED DESCRIPTION OF THE INVENTION

β-lapachone, as well as its intermediates, derivatives and analogs thereof (also referred to herein as the "active compounds"), are described in Li, C. J. et al., *J Biol. Chem.*, 1993. Unlike prior art β-lapachone syntheses as illustrated in Scheme 1, the synthesis of β-lapachone, in accordance with the present invention and generally illustrated in Scheme 2, commences with the reaction of 2-hydroxy-1,4-naphthoquinone with 1-bromo-3-methyl-2-butene in the presence of sodium iodide and triethylamine (a weak base) in dimethylsulfoxide (DMSO) to produce lapachol in up to 40% yield, after purification (20 g, up to 40% overall yield). Lapachol is then quantitatively converted to β-lapachone by treatment with sulfuric acid. The β-lapachone is purified by recrystallization from ethanol.

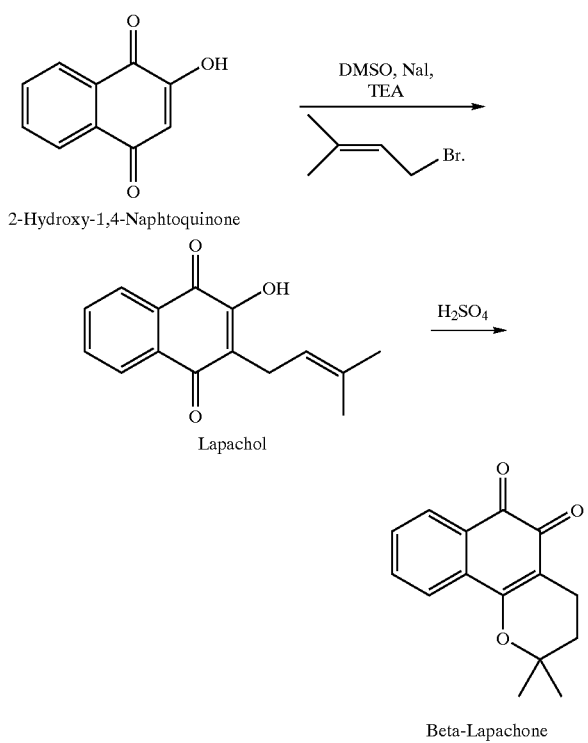

Scheme 2

Any impurities detected by thin layer chromatography (TLC), nuclear magnetic resonance spectroscopy (NMR) or HPLC (high pressure liquid chromatography) can be removed by addition of repeated crystallization steps.

Figure 1:
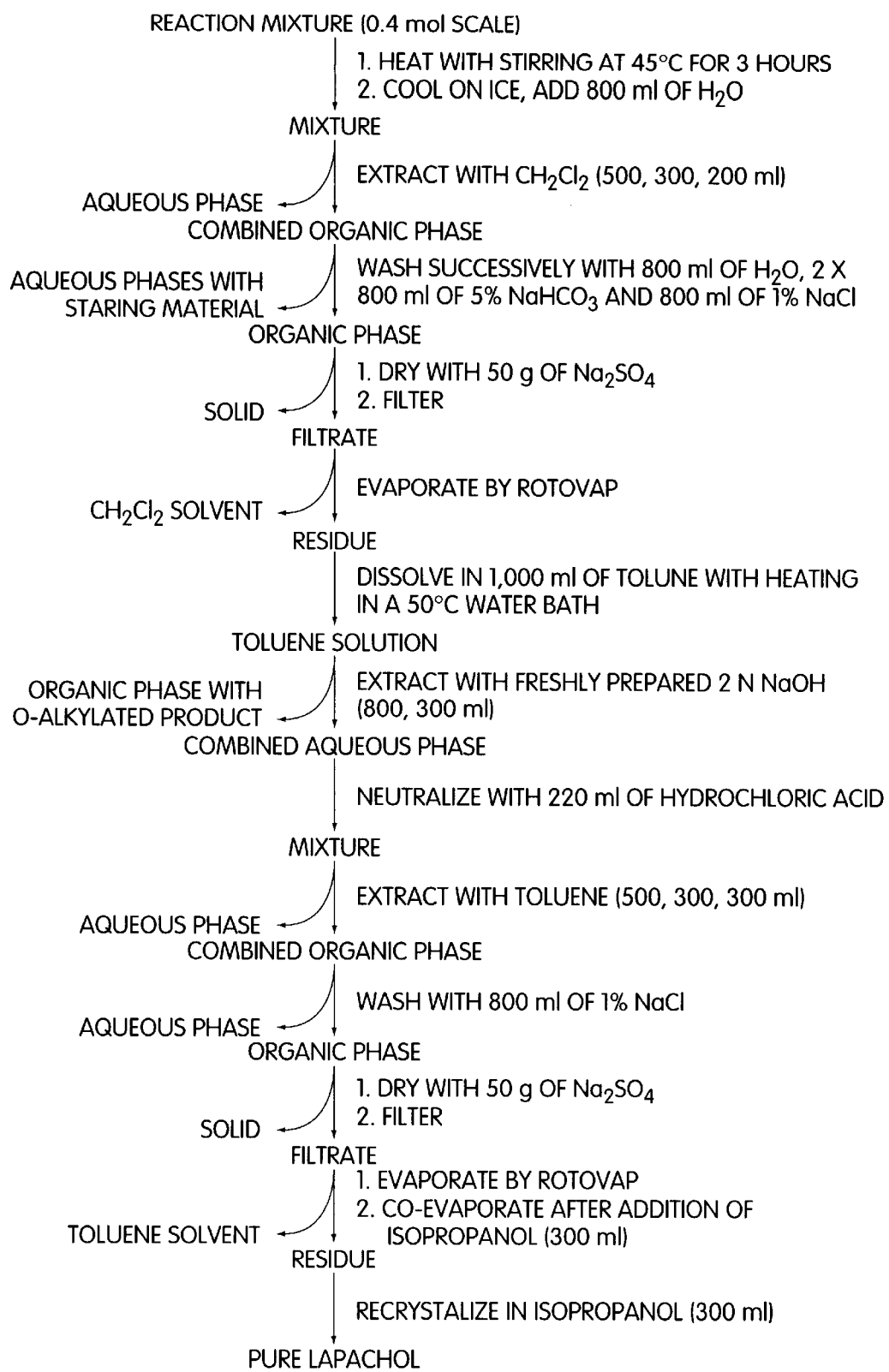
FIG. 1 is a schematic diagram that generally depicts the synthetic process of the present invention for the production of lapachol.

With reference to FIG. 1, and discussed in greater detail in the Examples section below, the synthetic process for preparing the β-lapachone intermediate, lapachol, commences with the preparation of a reaction mixture comprised of 2-hydroxyl-1,4-napthoquinone, 1-bromo-3-methyl-2-butene, triethylamine (TEA) and dimethylsulfoxide (DMSO). This reaction mixture is first stirred at room temperature under a noble gas atmosphere for about one hour. The reaction mixture is then heated and subsequently cooled to stop the reaction The mixture is then extracted three times with $CH_2Cl_2$ (e.g., 500 ml, 300 ml, 200 ml) and the organic phases pooled and successively washed with water, followed by two washings with 5% sodium bicarbonate ($NaHCO_3$) and one washing with 1% sodium chloride (NaCl). The organic phase is then dried with sodium sulfate ($Na_2SO_4$) and the filtrate, after filtration, is evaporated by Rotovap. The residue is then dissolved in toluene heated in a water bath at 50° C. and any existing insoluble material is filtered off. The resulting toluene solution is then extracted three times with 2 N NaOH (e.g., 800 ml, 300 ml, 200 ml). The resulting combined aqueous phase is then neutralized with 220 ml concentrated hydrochloric acid (HCl) and the mixture is extracted three times with toluene (e.g., 500 ml, 300 ml, 300 ml). The organic phases are then pooled and any (black) solids existing in the organic phase is removed by filtration. Once filtered, the combined organic phase is then washed successively with 1% NaCl, 5% aqueous sodium bicarbonate and 1% aqueous sodium chloride, the resulting organic phase is then dried with sodium sulfate and the resulting filtrate is evaporated by Rotovap to dryness, followed by the addition of isopropanol for co-evaporation to completely remove residual toluene. The residue is then dissolved in isopropanol, heated and then cooled. Pure lapachol is obtained after filtering washing with cold isopropanol and drying under vacuum.

Figure 2:
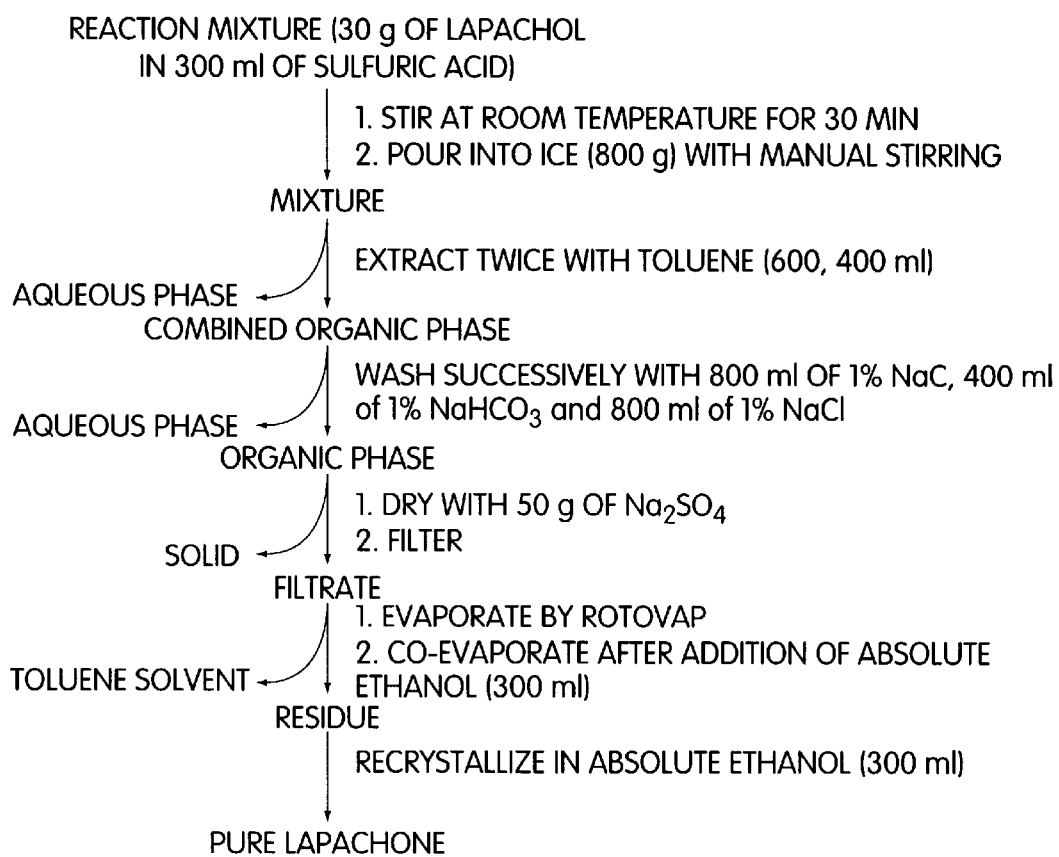
FIG. 2 is schematic diagram that generally depicts the synthetic process of the present invention for the production of β-lapachone.
Figure 3A:
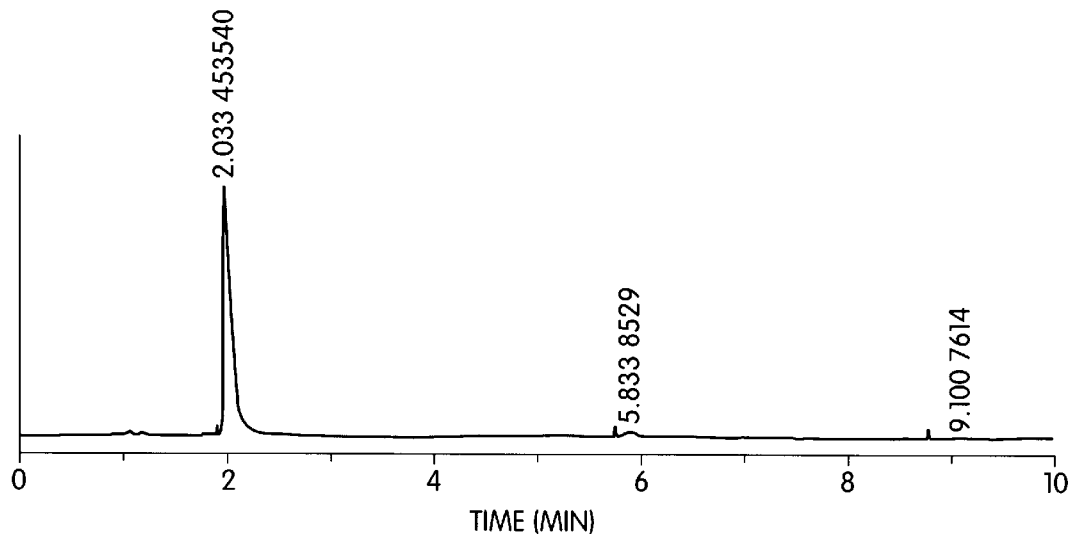
FIG. 3A is an HPLC chromatogram of 2-hydroxy-1,4-naphthoquinone (96.56%) at 252 nm.
Figure 3B:
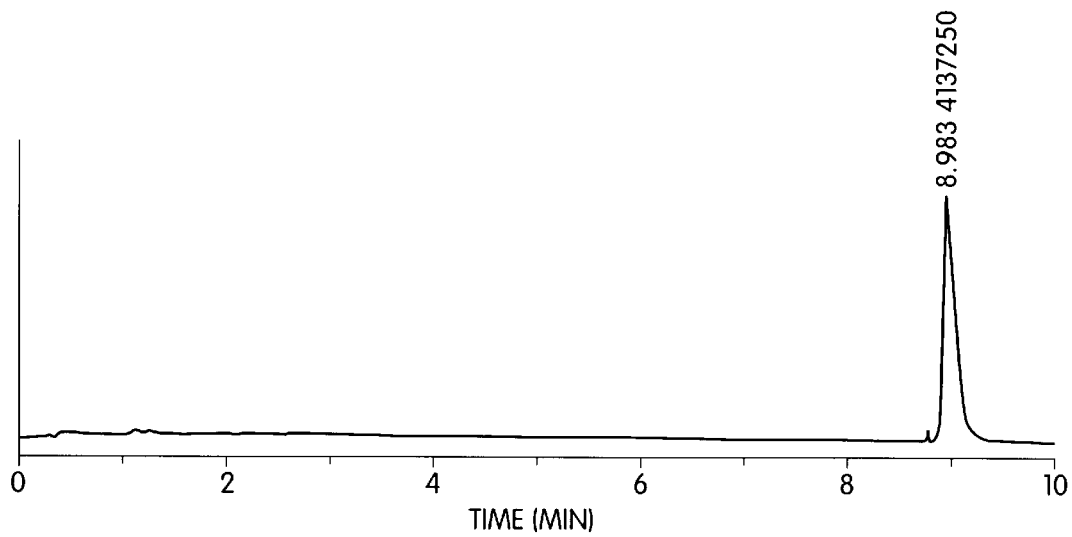
FIG. 3B is an HPLC chromatogram of lapachol (100%) at 252 nm prepared in accordance with the synthesis of the present invention.
Figure 3C:
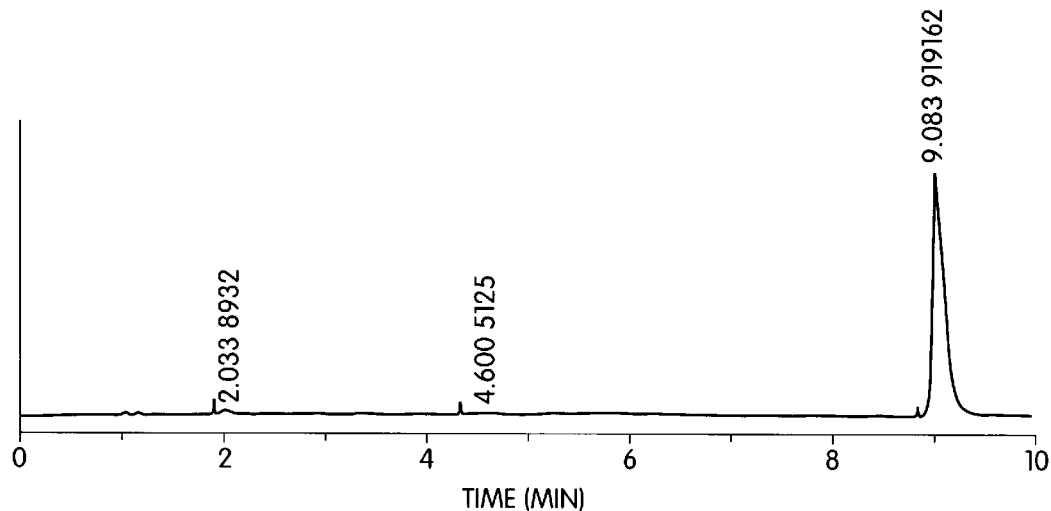
FIG. 3C is an HPLC chromatogram of lapachol sample with 1% of 2-hydroxy-1,4-naphthoquinone (starting material, 0.96%; second impurity peak, 0.55%; lapachol peak, 98.49%)
Figure 3D:
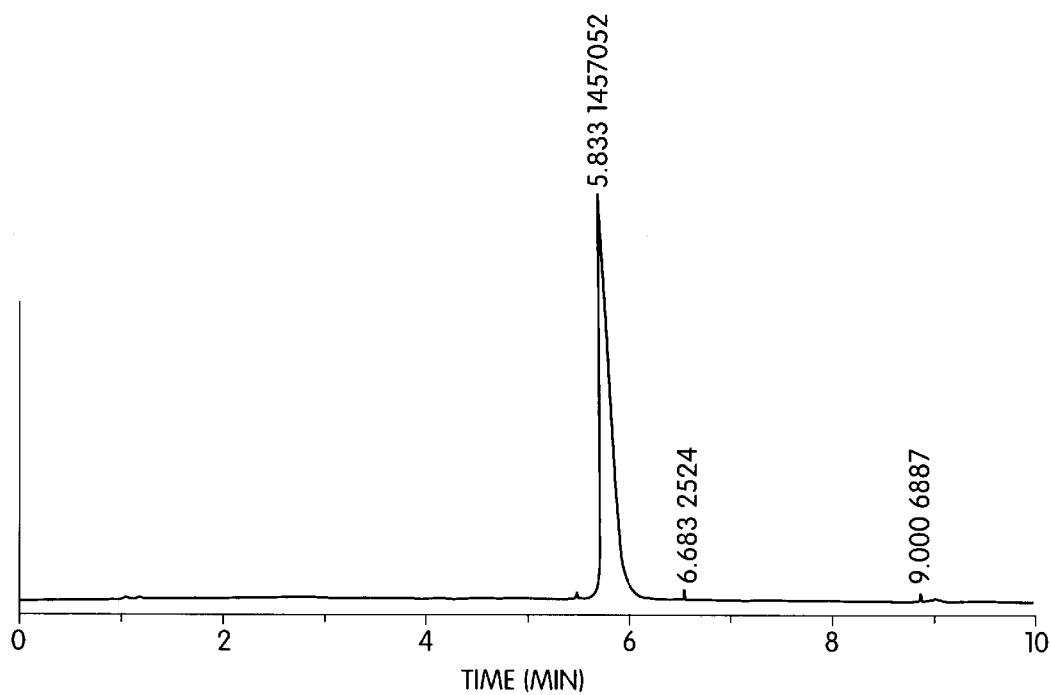
FIG. 3D is an HPLC chromatogram at 258 nm of β-lapachone (99.36% β-lapachone, 0.17% unknown peak, 0.47% lapachol)
Figure 3E:
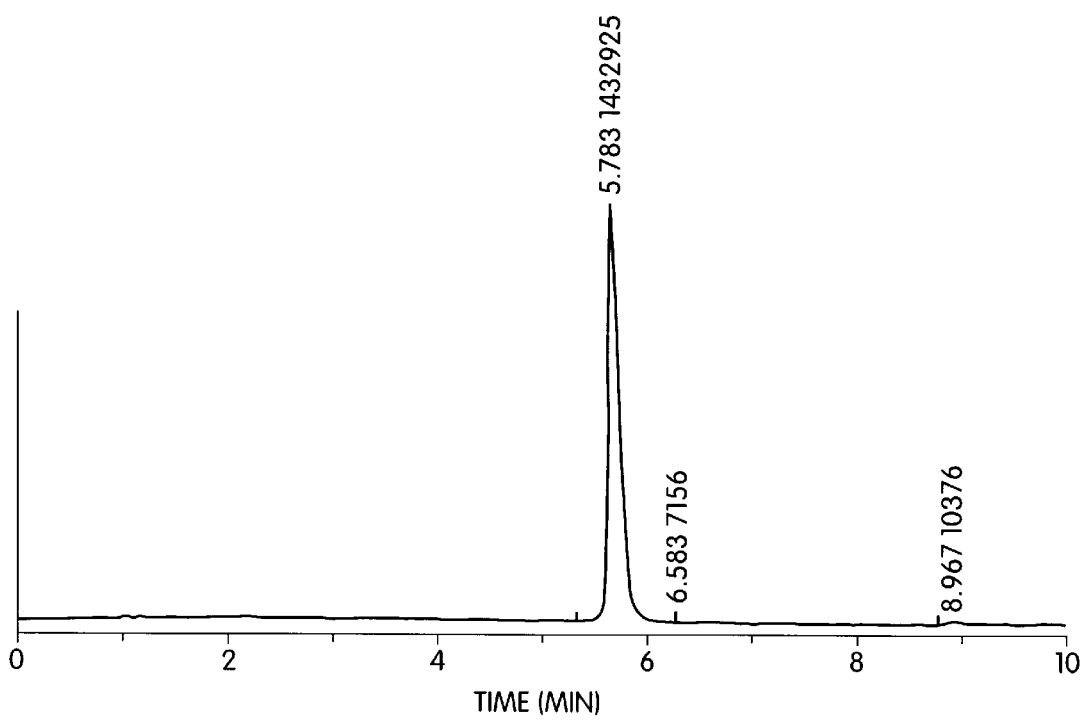
FIG. 3E is an HPLC chromatogram at 258 nm of β-lapachone sample with 1% lapachol (98.70% β-lapachone, 0.37% unknown material, 0.93% lapachol)

With reference to FIG. 2, and discussed in greater detail in the Examples section below, the synthesis of β-lapachone from lapachol commences with preparation of a reaction mixture comprised of the pure lapachol (30 g) in 300 ml of sulfuric acid. The reaction mixture is stirred at room temperature for 30 minutes and poured into ice water with manual stirring. The mixture is then extracted twice with toluene (e.g., 600 ml and 400 ml) to provide a combined organic phase, which is then washed successively with 800 ml of 1% NaCl, 400 ml of 1% $NaHCO_3$ and 800 ml of 1% NaCl. The resulting organic phase is then dried with 50 g $Na_2SO_4$ and the solid is filtered off. Tolune in the remaining filtrate is then evaporated off by Rotovap and co-evaporated following the addition of ethanol to completely remove residual toluene. The residue is then dissolved in either 75% ethanol or absolute ethanol, preferably absolute ethanol, heated in an 80° C. water bath and then filtered and cooled to 4° C. Pure β-lapachone is then isolated by filtration and washed with cold 75% ethanol (4° C. 100 ml), dried under vacuum, packed under Argon atmosphere and stored at −20° C. in the dark.

The invention is further defined by reference to the following examples. It will be apparent to those skilled in the art that many modifications, both to the materials and methods, may be practiced without departing from the purpose and interest of the invention.

EXAMPLES

1. Preparative Synthesis of Lapachol

Into a dried 2,000 ml round bottomed flask was added 2-hydroxy-1,4-napthoquinone (69.7 g, 0.40 mol), 1-bromo-3-methyl-2-butene (66 g, 0.44 mol), sodium iodide (60 g, 0.4 mol), triethylamine (58.55 ml, 0.42 mol) and dimethylsulfoxide (DMSO), 500 ml. The mixture was stirred vigorously at room temperature under Argon atmosphere for 1 hour, then heated with a heating mantle to 45° C. After 3–6 hours, at 45° C. with vigorous stirring, the mixture was cooled down in an ice bath, and 800 ml of water was added to stop the reaction. The mixture is then transferred into a 2,000 ml separatory funnel and extracted three times with methylene chloride (500 ml, 300 ml and 200 ml). The organic phases were pooled and washed successively with water (800 ml), 5% aqueous sodium bicarbonate (2×800 ml)* and 1% aqueous sodium chloride (800 ml), then dried with sodium sulfate (50 g). After filtration, the filtrate was evaporated to dryness by Rotovap. The residue was dissolved in toluene (1,000 ml) with heating in a 50° C. water bath, and any insoluble material existing was filtered off. The warm toluene solution was extracted three times with freshly prepared, warm 2N sodium hydroxide (800 ml, 300 ml and 200 ml). The aqueous phases were pooled and neutralized by addition of hydrochloric acid (220 ml) with vigorous manual stirring, then extracted three times with toluene (500 ml, 300 ml and 300 ml). The organic phase were pooled and any black solid existing in the organic phases was removed by filtration. The combined organic phase was washed successively with 1% aqueous sodium chloride (800 ml), 5% aqueous sodium bicarbonate (500 ml) and 1% aqueous sodium chloride (800 ml), and then dried with sodium sulfate (50 g). After filtration, the filtrate was evaporated to dryness by Rotovap, then isopropanol (300 ml) was added for co-evaporation to completely remove residual toluene. The residue was dissolved in isopropanol (300 ml) with heating in an 80° C. water bath and then was cooled to 4° C. slowly. Pure lapachol was obtained after filtering, washing with cold isopropanol (4° C., 50–100 ml) and drying under vacuum.

During the 5% aqueous sodium bicarbonate extractions, significant amounts of precipitate (2-hydroxy-1,4-naphthoquinone) appeared between aqueous phase and organic phase. The precipitate along with organic layer was separated from aqueous layer for the first extraction, but the precipitate was separated from both aqueous and organic layers for the second extraction, and was transferred into a 500 ml separatory funnel; 5% aqueous sodium bicarbonate (150 ml) and methylene chloride (150 ml) were added into the 50 ml separatory funnel. After shaking, the organic phase was separated and pooled with the major organic phases before extraction with 1% aqueous sodium chloride.

2. Preparative Synthesis of β-lapachone

Into a 1,000 ml beaker containing sulfuric acid (300 ml), lapachol (30 g, 0.124 mol) was added in portions slowly over 5 minutes at room temperature while stirring vigorously. After addition, the dark mixture was stirred for an additional 30 min and then poured into ice water (800 g) with manual stirring in a 2,000 ml beaker. The mixture was transferred into a 2,000 ml separatory funnel and extracted twice with toluene (600 ml and 400 ml). The toluene phases were pooled and washed successively with 1% aqueous sodium chloride (800 ml), 1% aqueous sodium bicarbonate (400 ml) and 1% aqueous sodium chloride (800 ml), and then dried with sodium sulfate (50 g). After filtration, the filtrate was evaporated to dryness by Rotovap and then ethanol (300 ml) was added for co-evaporation to completely remove residual toluene. The residue was dissolved in 75% ethanol or absolute ethanol, preferably absolute ethanol (ethanol/water, 3:1, 300 ml) with heating in an 80° C. water bath, then was filtered and cooled to 4° C. slowly. Pure β-lapachone was isolated by filtration, then washed with cold 75% ethanol (4° C., 100 ml), dried under vacuum, packed under Argon atmosphere and stored at −20° C. in the dark.

3. Analysis of Lapachol and β-lapachone

Routine procedures were used for melting point measurement, HPLC analysis and NMR analysis. Melting point and NMR data reported in literature were used for comparison with obtained data (see Tables 2 and 3 below). For HPLC analysis, a linear gradient from 25% to 75% buffer (methanol/acetonitrile/0.1% phosphoric acid (25:55:20)) in 10 min at a flow rate of 1 ml/min was applied, and the sample was prepared by dissolving lapachol or β-lapachone in methanol at a concentration of 2 mg/ml and then diluting it in methanol/acetonitrile/0.1% phosphoric acid (25:20:55) to 10 μg/ml for 10 to 100 μl injections. Methanol was Fisher Scientific cat #A452-4. Acetonitrile was Fisher Scientific cat #A998sk-4. Phosporic acid was Baker cat #0260-03. The HPLC column used was a Nova-Pak C18 (5 micron), 3.9×150 mm (Waters Part No. WAT086344), and the HPLC system used was a Beckman 126N Solvent Module/168NM Detector/System Gold.

In the lapachol synthesis, a weak organic base, triethylamine (TEA) was used (pyridine may also be used) instead of strong inorganic bases such as potassium hydroxide or lithium hydroxide as used in prior art lapachol syntheses to trap the acid generated from the reaction between the quinone and bromide compound (See Schaffner-Sabba, K., et al., β-Lapachone: Synthesis of Derivatives and Activities in Tumor Models, *J. Med. Chem.*, 27, (1984) 990–994; Sun, J. S. et al., A Preparative Synthesis of Lapachol and Related Naphthoquinones, *Tetrahedron Letters,* 39 (1998) 8221–8224).

Observation showed that use of a weak organic base simplified the procedures and enhanced the yield (see Scheme 1 above and Table 1 below), thus reducing production costs. The second step of the synthesis, conversion of the lapachol to β-lapachone, was shown to be relatively simple and resulted in high yield (more than 90%). The analytical data shown in Table 2 (melting point data for lapachol and β-lapachone) and Table 3 (NMR data for β-lapachone) confirm the identity of the synthesized compounds. HPLC analysis of starting material (2-hydroxy-1, 4-naphtoquinone), lapachol and β-lapachone prepared in accordance with the present method are more than 99% pure. See FIGS. 3A–3E.

TABLE 1

Lapachol Yields with Different Synthesis Methods

|  | Potassium Salt Method (Old) | Lithium Salt Method (Old) | Triethylamine Method (New) |
|---|---|---|---|
| Prep. 1 | 20.3% | 27.5% | 41.0% |
| Prep. 2 | 18.2% | 35.0% | 31.0% |
| Prep. 3 | ND | 26.6% | ND |

TABLE 2

Melting Point Date for Lapachol and β-lapachone

|  | Triethylamine Method | Reference Value (from Potassium Salt Method) |
|---|---|---|
| Lapachol | 138–139° C. | 136–137° C. |
| β-lapachone | 153–154° C. | 153–154° C. |

TABLE 3

NMR Data for β-lapachone

| Triethylamine Method | Reference Value (from Potassium Salt Method) |
| --- | --- |
| 1.47(s, 6-CH₃), 1.86(t, J=7, 2H3), 2.58(t, J=7, 2H-4), 7.4–8.2(m, H-7 to H-10) | 1.4(s, 6-CH₃), 1.82(t, J=7, 2H3), 2.57(t, J=7, 2H-4), 7.2–8.40(m, H-7 to H-10) |

EQUIVALENTS

While there have been shown and described and pointed out fundamental novel features of the invention as applied to preferred embodiments thereof, it will be understood that various omissions and substitutions and changes in the form and details of the disclosed invention may be made by those skilled in the art without departing from the spirit of the invention. It is the intention, therefore, to be limited only as indicated by the scope of the claims appended hereto.

What is claimed is:

1. A method for the synthesis of β-lapachone comprising the steps of:
   a. reacting 2-hydroxy-1,4-naphthoquinone with 1-bromo-3-methyl-2-butene in the presence of sodium iodide, dimethylsulfoxide and an amine base to form lapachol; and
   b. reacting the lapachol with sulfuric acid to provide β-lapachone.

2. The method according to claim 1, wherein the amine base is selected from the group consisting of triethylamine, pyridine, trimethylamine, N,N-diisopropylethylamine, or 2,6-lutidine.

3. The method according to claim 2, wherein the amine base is triethylamine.

4. The method according to claim 1, further comprising the step of purifying the β-lapachone by recrystallization with ethanol.

5. The method according to claim 4, wherein the recrystallization may be repeated to enhance the purity of said β-lapachone.

6. A method for the synthesis of lapachol comprising the step of reacting 2-hydroxy-1,4-naphthoquinone with 1-bromo-3-methyl-2-butene in the presence of sodium iodide, dimethylsulfoxide and an amine base.

7. The method according to claim 6, wherein the amine base is selected from the group consisting of triethylamine or pyridine.

8. The method according to claim 7, wherein the amine base is triethylamine.

9. A method for the synthesis of β-lapachone, the method comprising the steps of:
   a. synthesizing lapachol according to the method of claim 6;
   b. converting the lapachol into a β-lapachone product by reacting said lapachol with sulfuric acid; and
   c. purifying the β-lapachone product via crystallization.

10. The method according to claim 9, wherein the amine base is selected from the group consisting of triethylamine or pyridine.

11. The method according to claim 10, wherein the amine base is triethylamine.

12. A method for the synthesis of β-lapachone comprising the steps of:
   a. synthesizing a β-lapachone intermediate having the structure:

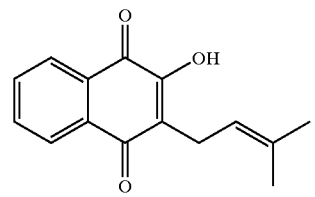

by reacting 2-hydroxy-1,4-naphthoquinone having the structure:

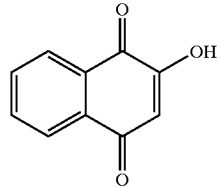

with 1-bromo-3-methyl-2-butene in the presence of sodium iodide, dimethylsulfoxide and triethylamine.
   b. converting the β-lapachone intermediate into β-lapachone by reacting the β-lapachone intermediate with sulfuric acid; and
   c. purifying the β-lapachone by crystallizing in ethanol and drying under vacuum.

13. A method for the synthesis of β-lapachone comprising the step of reacting lapachol with sulfuric acid.

14. A method for synthesis of lapachol comprising the step of reacting 2-hydroxy-1,4-naphthoquinone with 1-bromo-3-methyl-2-butene in the presence of sodium iodide, dimethylsulfoxide and triethylamine.

15. The method according to claim 14, wherein the lapachol is reacted with sulfuric acid to provide β-lapachone.

* * * * *